United States Patent [19]
McClatchie et al.

[11] Patent Number: 4,829,183
[45] Date of Patent: May 9, 1989

[54] DUAL SAMPLE CELL GAS ANALYZER

[75] Inventors: Edward A. McClatchie, Orinda; Kevin G. Williams, Pinole, both of Calif.

[73] Assignee: Andros Analyzers Incorporated, Berkeley, Calif.

[21] Appl. No.: 96,169

[22] Filed: Sep. 11, 1987

[51] Int. Cl.$^4$ ............................................. G01N 21/61
[52] U.S. Cl. .................................. 250/346; 250/339; 250/345; 250/352
[58] Field of Search ............... 250/345, 343, 344, 346, 250/339, 352

[56] References Cited

U.S. PATENT DOCUMENTS

| | | | |
|---|---|---|---|
| 2,666,854 | 1/1954 | Hutchins | 250/346 |
| 3,544,789 | 12/1970 | Wieder | 250/373 |
| 3,718,429 | 2/1973 | Williamson, Jr. | 250/343 |
| 3,893,770 | 7/1975 | Takami et al. | 250/345 |
| 3,947,685 | 3/1976 | Meinel | 250/343 |
| 4,355,233 | 10/1982 | Warnke et al. | 250/343 |
| 4,560,873 | 12/1985 | McGowan et al. | 250/339 |

Primary Examiner—Carolyn E. Fields
Attorney, Agent, or Firm—Fitch, Even, Tabin & Flannery

[57] ABSTRACT

A non-dispersive infrared gas analyzer is disclosed that accurately measures the concentration levels of a plurality of gases within a gas mixture. The analyzer includes first and second sample cells and is utilized advantageously for the measurement of $NO_x$ and hydrocarbon gas present in the exhaust of an automobile engine. The gas mixture of the exhaust is chilled before entering the first sample cell to remove a substantial amount of the water vapor from that sample cell to facilitate measurement of the $NO_x$ gas. The second sample cell receives the gas mixtue in an unchilled state to allow for accurate measurement of the hydrocarbon gas. The analyzer includes processors which are utilized to further correct the $NO_x$ measurement and which also interact with each other to provide an output data stream that is representative of the concentration levels of the gases that are being analyzed.

7 Claims, 2 Drawing Sheets

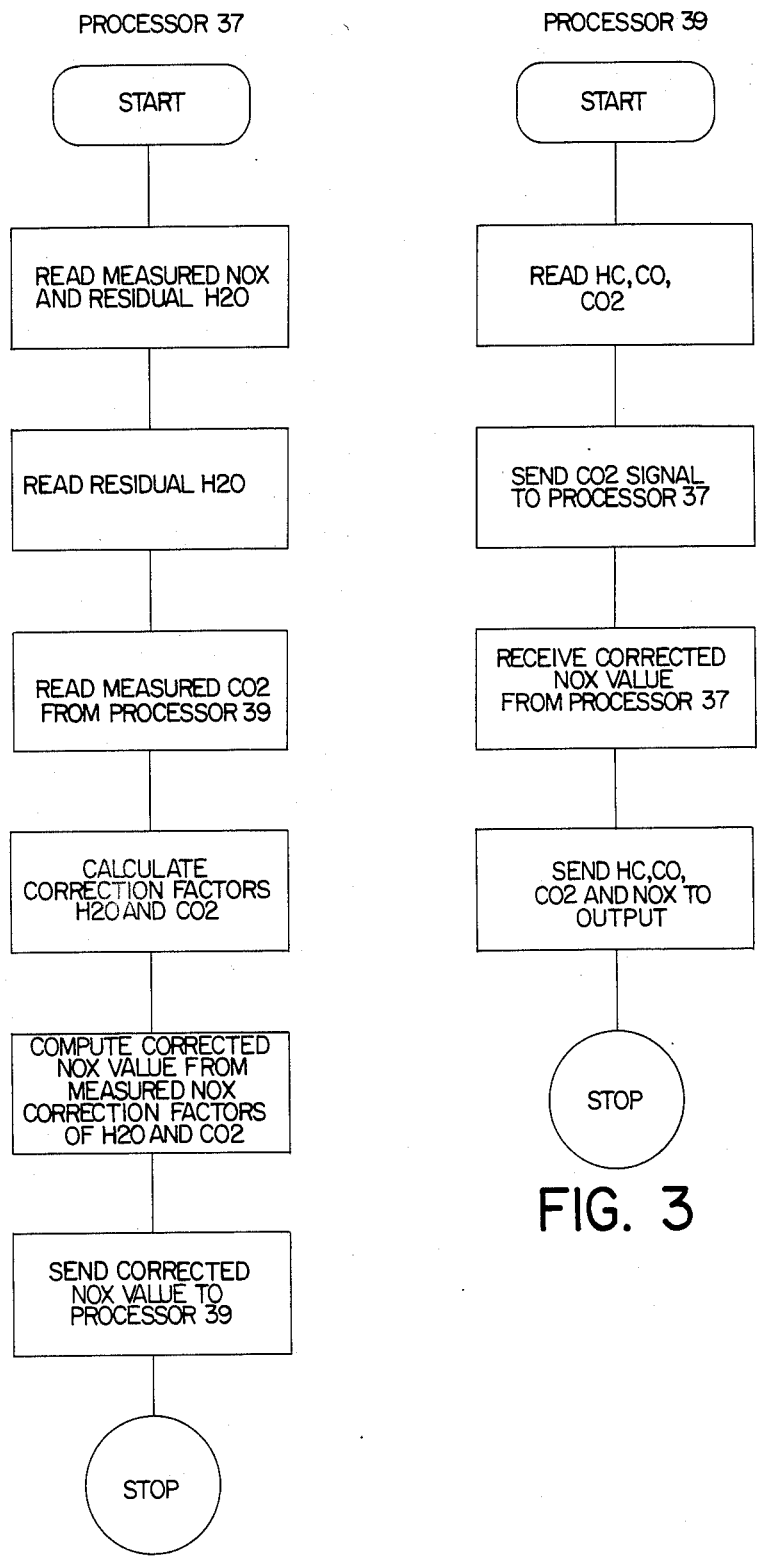

DUAL SAMPLE CELL GAS ANALYZER

FIELD OF THE INVENTION

The present invention relates to infrared gas analyzers and more particularly to an improved gas analyzer including means to accurately measure the plurality of gases within the exhaust of an automobile engine.

BACKGROUND OF THE INVENTION

Infrared gas analyzers of the type contemplated by the present invention typically employ an infrared source to pass infrared energy through an unknown gas mixture in a sample cell. Such gas analyzers operate on the principle that various gases exhibit a substantial absorption characteristic at specific respective wavelengths in the infrared radiation spectrum. The energy passing through the sample cell is detected to produce an electrical signal representative thereof. The resulting signal for each gas to be monitored in the analyzer is converted to an output indicating the concentration of the respective gases in the sample cell. Gas analyzers of this type are shown and described respectively in U.S. Pat. No. 4,013,260 issued on Mar. 22, 1977 and in U.S. Pat. No. 4,346,296 issued on Aug. 24, 1982, both assigned to the assignee of the present invention.

Gas analyzers such as those disclosed in the above references employ a beam of infrared energy passing through the sample cell containing an unknown gas mixture, the infrared energy beam being varied by the position of one or more filters in the path of the light beam. Typically, each filter passes only radiation at a characteristic absorption wavelength for a respective gas of interest. One or more additional filters may also be used as reference filters at wavelengths close to the characteristic absorption wave length for any gas present in the sample cell.

A simplified gas analyzer may also use a stationary filter or multiple filters with associated detectors rather than rotary filter wheel as described above. Such analyzers cause an AC signal to be produced by the detector by periodically interrupting the infrared beam, for example with a rotary chopper wheel.

It is known that ambient condition variations such as temperature, pressure, humidity and the like can adversely affect the accuracy of the measurements taken by gas analyzers. Certain inventions have been made to address these concerns. For example, U.S. Pat. No. 4,398,091 issued to Passaro entitled "Temperature Compensated Gas Analyzer" describes a gas analyzer that utilizes various means for compensating for temperature variations that improve the accuracy of the analyzer. Passaro discloses a preamplifier which is coupled to the output of each detector in the analyzer. The preamplifier includes adjustment means for correcting errors resulting from variations in the ambient or operating temperature of the detector. Passaro also teaches means for compensating for variations in the ambient or operating temperature of the sample cell itself. In this regard, an output amplifier within the processing circuit includes an adjustable means to produce offsetting compensation in the output amplifier to correct for the temperature variations in the sample cell.

Apparatus disclosed in the prior art shows the use of more than one gas cell in a gas analyzer. For example, a gas analyzer that has two cells is described in U.S. Pat. No. 3,529,152 in the names of J. P. Strange, et al. entitled, "Infrared Radiation Detection Device for a Non-Dispersive Selective Infrared Gas Analysis System." Strange, et al. disclose a non-dispersive gas analyzer wherein a pair of infrared sources produce energy in two separate beams, one of which is sent through a reference cell and the other of which is directed through a sample cell. The infrared energy in each of the beams is modulated and detected by separate detectors which produce output signals representative of the infrared energy passing through each of the cells. These two resulting signals are then processed together to produce an indication of the composition of the gas in the sample cell.

In a gas analyzer of this type, the reference cell contains a gas mixture that includes a known percentage of a particular gas to be analyzed. By comparing the intensity of the infrared energy passing through the gas mixture contained within the reference cell with the intensity of the infrared energy passing through the gas contained within the sample cell, processing electronics can derive the percentage of unknown gas in the sample cell gas mixture with a high degree of accuracy.

Although all of the above-mentioned gas analyzers work effectively for their intended purposes, they all suffer from a common deficiency when analyzing certain types of gas mixtures. More particularly, these analyzers are not as effective when measuring for the presence of gases in a gas mixture when more than one of those gases absorb infrared energy at approximately the same frequencies.

To more fully explain the problems encountered when measuring a plurality of gases, the following discussion will be directed toward the measurement for the presence of a plurality of gases in the exhaust of an automobile engine. However, a person of ordinary skill in the art will recognize that the principles thereof can be applied to other types of gas mixtures and that application would be within the spirit and scope of the present invention.

In the exhaust gas mixture produced by an automobile engine, gases are measured to determine, for example, the percentage of pollutants that are being expended when the automobile is operating. Typically, the gas mixture is analyzed for the presence of hydrocarbons, carbon monoxide, carbon dioxide and $NO_x$. In the context of this application what is meant by $NO_x$ are the oxides of nitrogen present in the automobile exhaust. These may include NO, $NO_2$ and the like.

There is a particular difficulty in measuring the $NO_x$ gas using infrared absorption techniques due to two factors. Firstly, the water vapor ($H_2O$) present in typical automotive vehicle emissions absorbs infrared energy at approximately the same frequencies as that of the $NO_x$ gas. Since, water is a much stronger absorber of infrared energy than $NO_x$, its presence interferes with the accuracy of the measurement of $NO_x$ Secondly, because carbon dioxide ($CO_2$) also absorbs infrared energy at approximately the same frequency as $NO_x$ gas, its presence in the exhaust gas also interferes with the measurement of $NO_x$.

It is known that if the gas mixture entering the sample cell is dehumidified, typically by chilling the gas, a substantial part of the water vapor resident therein can be condensed out of the sample cell. However, such dehumidification of the sample cell will also condense out some of the heavier hydrocarbons present in the gas mixture. Hence, the measurement for the presence of hydrocarbons within the same cell would be inaccurate if the gas mixture entering the cell is dehumidified.

Therefore, there is a need for an infrared gas analyzer that can accurately measure for the presence of plurality of gases where the measurement of one gas is impeded by the presence of one or more other gases in the mixture. More particularly, there is a need for an infrared gas analyzer that can accurately measure for the presence of both $NO_x$ and hydrocarbons from the exhaust of an automobile engine.

It is an object of the present invention to provide an improved non-dispersive gas analyzer.

It is a further object of the present invention to provide a gas analyzer capable of measuring accurately the concentration levels of a plurality of gases within a gas mixture.

It is also an object of the present invention to provide a gas analyzer which can accurately measure the concentration level of both $NO_x$ and hydrocarbons from the exhaust of an automobile engine.

SUMMARY OF THE INVENTION

The present invention provides a dual sample cell non-dispersive gas analyzer comprising a first sample cell for containing a gas mixture to be analyzed for the presence of $NO_x$ gas, a second sample cell for containing said gas mixture to be analyzed for the presence of hydrocarbon gas, means for directing infrared energy through the first and second sample cells, and means for modulating the amplitude of the infrared energy.

The gas analyzer of the present invention also includes means for chilling the gas mixture that enters the first sample cell and a first detector for detecting the infrared energy passing through the chilled first sample cell at the characteristic absorption wavelength of the $NO_x$ gas and producing a first signal that is representative of the $NO_x$ gas. The gas analyzer also includes a second detector for detecting the infrared energy passing through the second sample cell at the characteristic absorption wavelength of the hydrocarbon gas and producing a second signal that is representative of the hydrocarbon gas. Finally, the gas analyzer includes a processor means that processes the first signal of the first detector means and the second signal of the second detector means to provide an indication of the $NO_x$ gas and the hydrocarbon gas in the gas mixture.

Hence, by utilizing two sample cells, providing the same gas mixture to both cells and chilling the mixture prior to it entering one of the sample cells, the concentration levels of both $NO_x$ and hydrocarbons can be accurately measured.

In a preferred embodiment, the analyzer also includes means for measuring the residual amount of water vapor in the chilled first sample cell and providing a correction signal that is representative of that residual amount of water vapor. The processor means utilizes the correction signal to provide a more accurate indication of the concentration level of the $NO_x$ gas.

In yet another preferred embodiment, the gas analyzer also includes a means for detecting the infrared energy passing through the second cell at the characteristic wavelength of the $CO_2$ gas and producing a signal that is representative of the concentration level of the $CO_2$ gas. The processor means respond to the $CO_2$ gas signal, the $H_2O$ correction signal and the $NO_x$ signal from the first detector to provide a more accurate indication of the concentration level of the $NO_x$ gas.

BRIEF DESCRIPTION OF THE DRAWINGS

The advantages of the present invention will become more apparent from the following detailed description and drawings in which:

FIG. 2 is a flow chart of the operation of a first processor in accordance with the present invention.

FIG. 3 is a flow chart of the operation of a second processor in accordance with the present invention.

DETAILED DESCRIPTION

Figure 1:
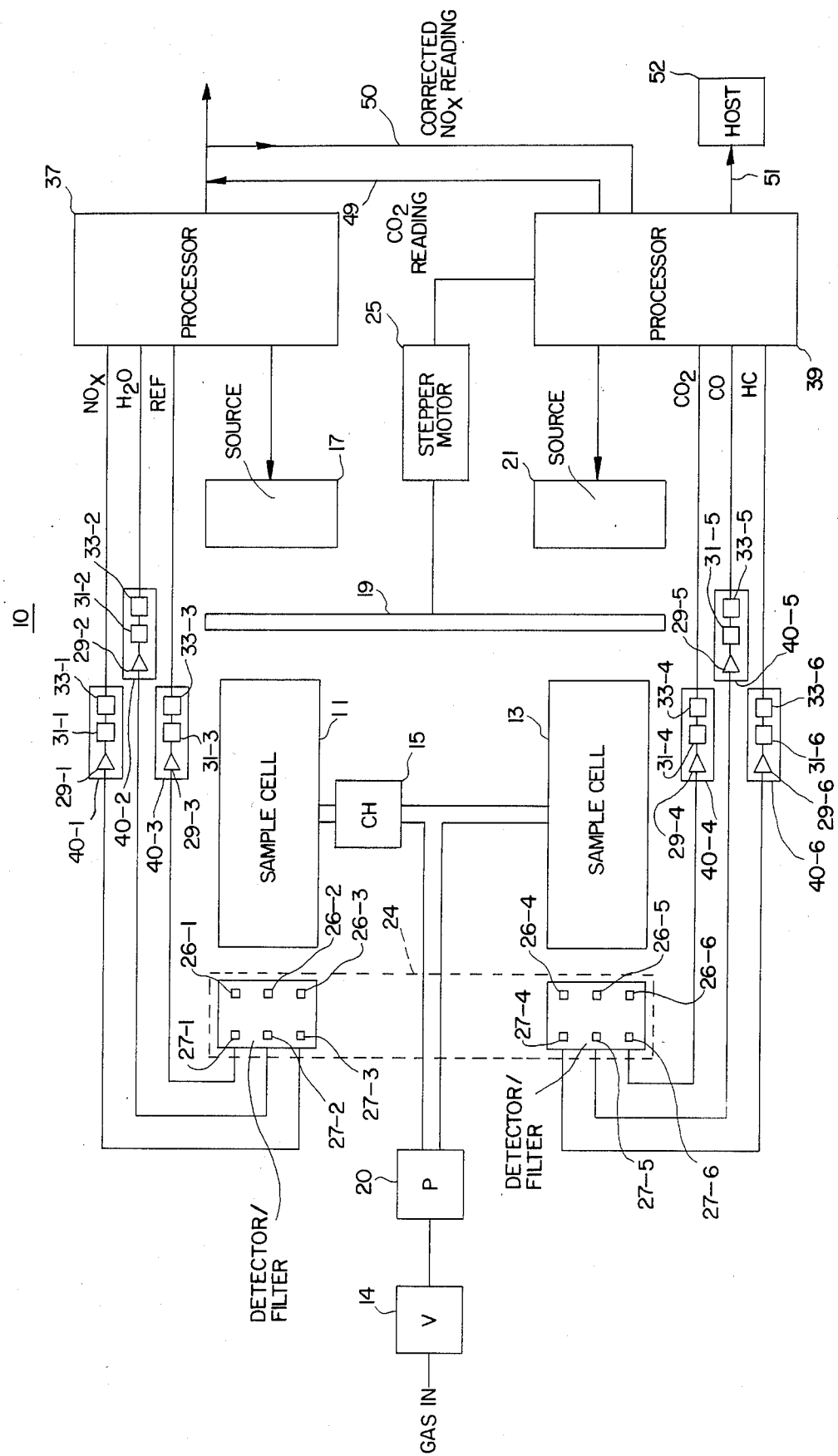
FIG. 1 is a diagram of a gas analyzer constructed in accordance with the present invention.

Shown in FIG. 1 is a diagram of the infrared gas analyzer 10 of the present invention. The gas analyzer 10 includes sample cells 11 and 13 that receive a gas mixture to be detected. The gas mixture entering sample cell 11 is dehumidified by chiller 15. Sample cells 11 and 13 each have respective sources 17 and 21 which direct infrared energy therethrough via chopper wheel 19. The chopper wheel 19 under control of processor 39 is actuated by stepper motor 25. The sources 17 and 21 are under the control of processors 37 and 39 respectively. A detector/filter assembly 24 receives the infrared energy exiting sample cells 11 and 13. Filters 26-1 through 26-3 receive energy from sample cell 11 and filters 26-4 through 26-6 receive energy from sample cell 13. Detectors 27-1 through 27-6 receive the filtered energy from 26-1 through 26-6 respectively and produce signal outputs representative thereof. The signals from detectors 27-1 through 27-6 are provided to gas channels 40-1 through 40-6.

The gas channels 40-1 through 40-6 are typically signal processors which present the AC signals to the processors 37 and 39 to allow for the conversion of the signal output to digital form. The gas channels 40-1 through 40-6 in conjunction with the processors 37 and 39 cooperate to convert the AC signals from the detectors 27-1 through 27-6 to DC signals which are representative of the concentration levels of the gases being measured. Gas channels 40-1 through 40-3 provide signals to processor 37. Gas channels 40-4 through 40-6 provide signals to processor 39. Processors 37 and 39 interact to provide an output signal representative of the concentration levels of the gases being measured.

The analyzer 10 operates in the following manner. A gas mixture, typically from an automobile engine exhaust, enters the gas analyzer 10 through valve 14 and then is pumped by pump 20 to the sample cells 11 and 13 respectively. As is also seen, the gas entering sample cell 11 is chilled or dehumidified by chiller 15.

Chiller 15 is a refrigeration unit that cools and dehumidifies the gas mixture to substantially reduce the water vapor resident therein. Typically, the exhaust gas mixture exiting an automobile engine contains 30,000 parts per million (ppm) of water vapor. The chiller 15 cools the gas mixture to between $-2°$ C. and $-20°$ C. to remove a substantial portion of the water vapor in the gas mixture through condensation. It has been found by lowering the temperature of the mixture to the above-mentioned levels, the water vapor content of the mixture will be reduced to approximately 1,000 ppm. As will be explained in detail hereinbelow, by removing a substantial portion of the water vapor, the accuracy in the measurement of another group of gases, namely $NO_x$, becomes significantly more accurate. Accordingly, the mixture entering sample cell 11 contains a residual amount of water vapor.

A first source 17 under control of processor 37 directs infrared radiation through first sample cell 11 and the infrared radiation is periodically interrupted by a chopper wheel or blade 19 at a predetermined frequency. Similarly, a second source 21 under control of processor 39 directs infrared radiation through sample cell 13 and the infrared radiation is also periodically interrupted by the chopper blade 19 at a predetermined frequency. Each of sources 17 and 21 typically comprises a ceramic element that generates infrared energy through resistive heating.

The chopper blade 19 is under control of processor 39 via stepper motor 25. Through the use of a stepper motor, the chopper blade 19 is rotated through discreet steps which provide for a sharp square wave AC signal output. The dwell time of the chopper blade 19 at each position is selected to provide a desired wave shape. Thus, the chopper blade 19 provides an AC signal which, as is shown in the art, has the effect of canceling out any background DC radiation. In a preferred embodiment, the chopper blade 19 comprises a wedged shaped metal blade encompassing 90° of a circle. The chopper blade 19 is rotated through a 90° excursion in such a manner so as to alternately block the infrared energy passing through sample cells 11 and 13. Thus an AC signal is created at the output of each sample cell 11 and 13. Of course, one ordinarily skilled in the art will recognize that other types of chopper blade configurations can be utilized to provide the same duty cycle.

Accordingly, in the illustrative embodiment of the present invention, detection signals are produced by the cooperation of filters 26-1, 26-2, 26-3 with detectors 27-1, 27-2, 27-3 corresponding to the infrared radiation received at a preselected wavelength of the gas within sample cell 11. Similarly, detection signals are produced by the cooperation of filters 26-4, 26-5, 26-6 with detectors 27-4, 27-5, 27-6 respectively corresponding to the infrared radiation received at a respective preselected wavelength of said gas mixture in sample cell 13.

Filters 26-1 through 26-6 and detectors 27-1 through 27-6 are preferably an individual assembly 24 in which an optical filter and a thermopile detector are utilized for each gas to be measured. It is known that the assembly 24 oftentimes includes a resistive heating element (not shown) and temperature sensor (not shown) to maintain the assembly 24 at a predetermined temperature and thereby eliminate drift corrections required when there are changes in the ambient environment.

The selection of the wavelengths of the respective gases to be detected are determined by respective narrow passband bandpass filters 26-1, 26-2, 26-3, 26-4, 26-5, and 26-6. The sources 17 and 21 produce the infrared energy that is filtered by filters 26-1 through 26-6. The filtered energy is then received by detectors 27-1 through 27-6, respectively.

The AC signal outputs of the detectors 27-1, 272, 27-3, 27-4, 27-5, 27-6 are processed by gas channels 40-1, 40-2, 40-3, 40-4, 40-5, 40-6, respectively to produce suitable signals and controls for analog to digital conversion by processors 37 and 39 respectively. These converted signals are systematically related to the concentration of the gas to be detected.

Accordingly, each AC signal received via sample cell 11 is amplified by amplifiers 29-1, 29-2, 29-3, integrated by integrators 31-1, 31-2 and 31-3 and converted to digital format by processor 37 working in conjunction with control logic 33-1, 33-2 and 33-3. The digital words thus created are systematically related to the concentration of the three gases to be measured in the sample cell 11 (in this example $NO_x$, residual $H_2O$ and reference).

Each AC signal received via sample cell 13 is amplified by amplifiers 29-4, 29-5, 29-6, integrated by integrators 31-1, 31-2 and 31-3 and converted to digital format by processor 39 working in conjunction with control logic 33-4, 33-5 and 33-6. The digital words thus created are systematically related to the concentration of the three gases to be measured in the sample cell 13 (in this example $CO_2$, CO and HC).

The preferred embodiment of the present invention is utilized for detecting the relative presence of gases in the exhaust gas of an automobile engine. The gases of particular interest are hydrocarbons, carbon monoxide, and oxides of nitrogen, hereinafter designated $NO_x$. It is recognized however by one having ordinary skill in the art that the invention is not limited to use in connection with such specific gases nor is it limited to use in connection with the exhaust gas of an automobile engine. Accordingly, there will be many other uses, apparent to those skilled in the art, for the gas analyzer of the present invention.

A particular problem in measuring the relative percentages of gases in an exhaust gas of an automobile engine is that the gases because of their relative absorption characteristics can interfere with the measurements of each other. More particularly it is has been found that $NO_x$ gas has an absorption characteristic that is very similar to water vapor ($H_2O$), which is normally present in the exhaust gas of an automobile engine. As has been before mentioned, there is typically a large quantity of water vapor (approximately 30,000 ppm) in the exhaust gas. Since $H_2O$ is a stronger absorber of infrared emissions than $NO_x$, the $NO_x$ concentration level can be difficult to measure.

It is known that a substantial quantity of water vapor can be removed from the gas mixture by chilling the mixture before it enters the sample cell. However, this hinders the measurement of hydrocarbons because the heavier hydrocarbons will also be condensed out when the gas mixture is chilled.

The present invention solves this problem by utilizing two sample cells, wherein the gas mixture entering sample cell 11 is chilled which allows for the accurate measurement of the $NO_x$ concentration level within the sample cell 11 and wherein the gas mixture entering the second sample cell 13 is not chilled so that the hydrocarbon concentration level can be accurately measured.

The corresponding DC signal produced from both sample cells 11, 13 are delivered to the processors 37 and 39, respectively which interact to further refine the measurement of the $NO_x$ gas. Although dehumidification by chilling eliminates a substantial amount of the water vapor in the sample cell 11, it is known that a residual amount of water vapor will remain after the dehumidification process. Since the residual amount of water vapor remaining is so small (on the order of 1,000 ppm) then it is possible to utilize the residual water vapor reading to correct the measurement of $NO_x$ gas provided by gas channel 40-1 Hence, the processor 37 receives a residual water vapor signal from gas channel 40-2 and utilizes that signal to correct the $NO_x$ gas measurement of the analyzer.

As has been before-mentioned, the $CO_2$ measurement also interferes with the $NO_x$ measurement in sample cell 11. The $CO_2$ signal provided by gas channel 40-4 is presented to the processor 39 which passes the signal to processor 37 via line 49. Processor 37 thereafter utilizes the $CO_2$ signal to further correct the $NO_x$ measurement. In so doing, a $NO_x$ gas signal is provided on line 50 that more accurately represents the concentration level of $NO_x$ in the gas mixture.

After the corrected $NO_x$ gas mixture signal is provided to processor 39 via lead 50. Processor 39 responsive to signals received from channels 40-4, 40-5, 40-6, via sample cell 13 and the corrected $NO_x$ signal from the processor 37 provides an output data stream on line 51 representative of the concentration levels of carbon dioxide ($CO_2$), carbon monoxide (CO), hydrocarbon (HC) and oxides of nitrogen ($NO_x$). This digital output is presented to host computer 52, where it is formatted for presentation on appropriate display devices (not shown).

Processors 37 and 39 can be any type of digital processor that will perform the above-mentioned operations. A typical microprocessor that can be utilized to perform the functions of either processor 37 or processor 39 is Model Number 68HC11 which is manufactured by Motorola, Inc.

To more fully explain the operation of processors 37 and 39, refer to the flow charts of FIGS. 2 and 3. As is seen, processor 37 reads the $NO_x$ value and the residual $H_2O$ value. Simultaneously, processor 39 reads the hydrocarbon (HC), carbon monoxide (CO) and carbon dioxide ($CO_2$) values. The $CO_2$ value is sent from processor 39 to processor 37 and read into processor 37. Processor 37 calculates a corrected $NO_x$ value utilizing the $H_2O$ and $CO_2$ signals. Processor 37 thereafter sends the corrected $NO_x$ signal to processor 39. Processor 39 receives the corrected $NO_x$ and sends the corrected $NO_x$, the HC, $CO_2$ and CO signals to the host 52.

The residual $H_2O$ and $CO_2$ concentrations in sample cell 11 provides two sources of error in the measurement of $NO_x$ concentration. Since the infrared absorption residual spectrum of $NO_x$ contains an absorption band that is very close to the absorption band of the $H_2O$, the water vapor causes a spectral interference with the $NO_x$ measurement. As is well known, the presence of $CO_2$ causes the $NO_x$ absorption spectra to broaden and therefore results in an increased response of the analyzer 10 to the $NO_x$ signal causing it to be inaccurate.

In order to perform accurate measurements for the amount of $NO_x$ in the automobile exhaust gas mixture, the $CO_2$ signal and the residual $H_2O$ signal are utilized to correct the $NO_x$ measurement.

Accordingly, processor 37 utilizes carbon dioxide signal to eliminate the effect of the spectral line broadening error in the $NO_x$ measurement in conjunction with a suitable correction formula. In one example, a formula as follows will provide for correction for an error signal for the $CO_2$ reading:

$$E_{CO_2} = F(CO_{2m}) \qquad (1)$$

where $E_{CO_2}$ is the error signal provided by the $CO_2$ concentration level and $F(CO_{2m})$ is an equation relating the measured $CO_2$ concentration level to the spectral line broadening.

$E_{CO_2}$ is derived in accordance with empirical techniques. For example, a series of DC signals are produced by passing a plurality of known concentration levels of $CO_2$ through the sample cell 11. As is well known, each one of the plurality of concentration levels produces an output signal in the $NO_x$ channel 40-1 representative of the interference of that concentration of $CO_2$. The plurality of output signals are then mapped into processor 37 as an empirical equation from which an error correction factor $E_{CO_2}$ can be derived. Hence, when a signal is presented to processor 37 that represents a known percentage of $CO_2$ then it is input into the previously "mapped" equation. Through this computation the error correction signal $E_{CO_2}$ is obtained.

Similarly, the water vapor signal from gas channel 40-2 in conjunction with a suitable correction formula is utilized to correct the $NO_x$ measurement for the spectral interference error created by the water vapor. For example, a formula as follows will provide for correction for the $H_2O$ concentration;

$$E_{H_2O} = F(H_2O_m) \qquad (2)$$

where $^3H_2O$ is the error signal provided by the residual water vapor and $F(H_2O_m)$ is an equation relating the measured $H_2O$ concentration to the spectral interference.

$E_{H_2O}$ is derived in accordance with empirical techniques. For example, a series of DC signals are produced by passing a plurality of known concentration levels of $H_2O$ through the sample cell 11. As is well known, each one of the plurality of concentration levels produces an output signal in the $NO_x$ channel 40-1 representative of the interference of that concentration of $H_2O$.

The plurality of output signals are then mapped into processor 37 as an empirical equation from which an error correction factor ($E_{H_2O}$) can be derived. Hence, when a signal is presented to processor 37 that represents a known percentage of $H_2O$, then it is input into the previously "mapped" equation. Through this computation the error correction signal $E_{H_2O}$ is obtained.

Thereafter processor 37 utilizes the correction signals $E_{CO_2}$ and $E_{H_2O}$ to improve the accuracy of the $NO_x$ reading in accordance with formula (3) below:

$$NO_{xc} = NO_{xm} - (E_{CO_2} + E_{H_2O}) \qquad (3)$$

where $NO_{xc}$ is the corrected $NO_x$ signal and $NO_{xm}$ is the measured $NO_x$ signal.

One of ordinary skill in the art will recognize that there are various other methods of determining the spectral interference and spectral broadening errors introduced to the $NO_x$ concentration. Accordingly, the above-described formulas are for exemplary purposes only and one could utilize other methods and apparatus to correct for these errors.

Accordingly, referring back to FIGS. 2 and 3, the processor 37 utilizes both of the error signals $E_{CO_2}$ and $E_{H_2O}$ to correct the $NO_x$ concentration measurement. In so doing, a gas analyzer 10 is provided in which a measurement of both the $NO_x$ concentration level and the hydrocarbon concentration level can be accurately obtained.

The processor 37 then provides this corrected $NO_x$ measurement to the processor 39. The processor 39 thereafter provides an output data stream to a host 52 (FIG. 1) representative of the measurements of the corrected $NO_x$ measurement, the hydrocarbon measurement, the $CO_2$ measurement and the CO measurement.

Hence, it has been shown that through the interaction of the processors 37 and 39 with the remaining portions of the dual sample cell gas analyzer 10 a plurality of gases can be accurately measured even in those cases where the measurement of one gas may impede or interfere with the measurement of the remaining gases. More particularly, in the preferred embodiment of the present invention, water vapor is substantially removed from a first sample cell 11 by dehumidifying or chilling the gas mixture before entering the first sample cell 11. Dehumidifying the gas mixture substantially improves the accuracy of the measurement of the $NO_x$ gas in the mixture. The second sample cell, on the other hand, receives the gas mixture without being dehumidified. Hence, an accurate measurement of the hydrocarbons can be obtained from the gas mixture of the sample cell 13.

In a further improvement to the $NO_x$ gas measurement, the residual water vapor is thereafter detected in sample cell 11 and that measurement is processed with the measured $NO_x$ concentration level to provide an accurate indication of the concentration level of the $NO_x$ gas.

In a final improvement to the $NO_x$ gas measurement, $CO_2$ information is obtained from the unchilled gas mixture in the second sample cell 13 to further correct the $NO_x$ measurement. The corrected $NO_x$ measurement signal is sent along with signals representing the measurements of the HC, CO, $CO_2$ as part of an output data stream to the host 52 to provide the various concentration level readings.

In the present invention, it should be noted that the illustrative embodiment of the dual sample cell gas analyzer 10 can be modified in a variety of ways and those changes would be within the spirit and scope of the present invention. For example, the functions of processors 37 and 39 could be interchanged. It is also clear that processors 37 and 39 could be replaced by one processor that performs all of their functions. Finally, it is clear that devices or circuitry other than microprocessors can be utilized to perform the various operations on the signals to provide more accurate measurement.

One of ordinary skill will also recognize that the number of gas channels can be lesser or greater than the six shown in the illustrative embodiment. Finally, it is clear that gas mixtures other than the exhaust from an automobile engine can be measured and that measurement would be within the spirit and scope of the present invention. Accordingly, the scope of the invention is defined only by the following appended claims.

What is claimed is:

1. A non-dispersive gas analyzer comprising:
a first sample cell for containing a sample gas mixture to be analyzed for the presence of $NO_x$ gas; a second sample cell for containing said gas mixture to be analyzed for the presence of hydrocarbon gas;
means for directing infrared energy through said first and second sample cells;
means for modulating the amplitude of said infrared energy;
means for dehumidifying said gas mixture entering said first sample cell;
first detector means for detecting the infrared energy passing through the dehumidified gas mixture in said first sample cell at a characteristic absorption wavelength of said $NO_x$ gas and producing a first signal representative thereof;
second detector means for detecting the infrared energy passing through said second sample cell at a characteristic absorption wavelength of hydrocarbon gas and producing a second signal representative thereof;
processor means for processing said first signal of said first detector means to provide an indication of the concentration level of $NO_x$ gas in said gas mixture and for processing said second signal of said second detector means to provide an indication of the concentration level of hydrocarbon gas in said gas mixture; and
means for measuring a residual amount of water vapor within the dehumidified gas mixture in said first sample cell and for providing a correction signal representative thereof, wherein said processor means utilizes said correction signal to provide a more accurate indication of the concentration level of $NO_x$ gas.

2. The gas analyzer of claim 1 which further comprises;
means for detecting the infrared energy passing through said second sample cell at the characteristic wavelength of $CO_2$ gas and producing a signal representative thereof;
wherein said processor means is responsive to said $CO_2$ gas signal to correct said signal from said first detector means to provide a more accurate indication of the concentration level of $NO_x$ gas.

3. The gas analyzer of claim 2 in which said modulating means comprises;
a rotary chopper blade; and
a stepper motor for rotating said chopper blade through a plurality of position steps, each position step being of a predetermined duration.

4. The gas analyzer of claim 3 in which said processor means controls said stepper motor so as to cause said chopper blade to alternately block the infrared energy entering said first and second sample cells.

5. The gas analyzer of claim 2 in which said processor means further comprises;
a first processor for receiving and processing said first signal representative of $NO_x$ gas and said water vapor correction signal; and
a second processor for receiving and processing said second signal and said $CO_2$ gas signal; wherein said first processor receives said $CO_2$ gas signal from said second processor and processes said $CO_2$ gas signal, said water vapor correction signal and said $NO_x$ gas signal to provide an output signal indicative of the concentration level of $NO_x$ gas, and wherein said second processor receives said output signal from said first processor and provides an output data stream representative of $NO_x$ and hydrocarbon concentrations.

6. A non-dispersive gas analyzer comprising:
a sample cell for containing a first sample gas mixture to be analyzed for the presence of a predetermined gas;
means for directing infrared energy through said sample cell;
means for modulating the amplitude of said infrared energy;
means for dehumidifying the gas mixture entering said sample cell, said sample cell containing a residual amount of water vapor;
means for measuring said residual amount of water vapor and for producing a correction signal representative thereof;
means for detecting the infrared energy passing through said sample cell at the characteristic wavelength of said predetermined gas and producing an output signal representative thereof; and,
processor means for processing said correction signal with said output signal to provide a corrected output signal representative of the characteristic absorption wavelength of said predetermined gas.

7. A non-dispersive gas analyzer comprising:
a first sample cell for containing a sample gas mixture to be analyzed for the presence of a first predetermined gas;
a second sample cell for containing the sample gas mixture to be analyzed for the presence of a second predetermined gas;
means for directing infrared energy through said first nd second sample cells;
means for modulating the amplitude of said infrared energy;
first detector means for detecting the infrared energy passing through said first sample cell at a first characteristic absorption wavelength of said first predetermined gas and producing a first signal representative thereof;
second detector means for detecting the infrared energy passing through said second sample cell at a second characteristic absorption wavelength of said second redetermined gas and producing a second signal representative thereof;
processor means for processing said second signal of said second detector means to provide an indication of the concentration level of said second predetermined gas in said gas mixture, said processing means being responsive to said indication of the concentration level of said second predetermined gas and providing a correction signal representative of the interference of said second predetermined gas with said first predetermined gas; said processing means processing said first signal of said first detector means and said correction signal to provide an indication of the concentration level of said first predetermined gas in said gas mixture.
means for dehumidifying said gas mixture entering said first sample cell, said first sample cell containing a residual mount of water vapor; and
means for measuring the residual amount of water vapor and providing a measurement signal representative thereof;
wherein said processor means utilizes said measurement
signal to provide a more accurate indication of the concentration level of said second predetermined gas.

* * * * *

UNITED STATES PATENT AND TRADEMARK OFFICE
CERTIFICATE OF CORRECTION

PATENT NO. : 4,829,183

DATED : May 9, 1989

INVENTOR(S) : Edward A. McClatchie

It is certified that error appears in the above-identified patent and that said Letters Patent is hereby corrected as shown below:

Column 2, line 57, after "$NO_x$" insert --.--.

Column 5, line 56, "272" should be --27-2--.

Column 6, line 61, after "40-1" insert --.--.

Column 8, line 15, "$^3H_2O$" should be --$^EH_2O$--.

Column 9, line 60, "said" should be deleted.

Column 11, line 12, "nd" should be --and--.

Column 11, line 24, "redetermined" should be --predetermined--.

Column 12, line 16, "mount" should be --amount--.

Column 12, there should be no paragraph space between lines 21-22.

Signed and Sealed this

Fourteenth Day of May, 1991

Attest:

HARRY F. MANBECK, JR.

*Attesting Officer*     *Commissioner of Patents and Trademarks*